United States Patent [19]

Kent et al.

[11] Patent Number: 4,548,904

[45] Date of Patent: Oct. 22, 1985

[54] PROTEIN SEQUENCING METHOD

[75] Inventors: Stephen B. H. Kent; James J. L'Italien, both of Edina, Minn.

[73] Assignee: Molecular Genetics Research & Development, Minnetonka, Minn.

[21] Appl. No.: 446,579

[22] Filed: Dec. 3, 1982

[51] Int. Cl.[4] ............................................. G01N 33/68
[52] U.S. Cl. .................................... 436/89; 436/161; 436/172; 436/176
[58] Field of Search ................... 422/63, 64, 116, 131; 436/89, 172, 175, 176, 178, 180, 161, 162

[56] References Cited

PUBLICATIONS

Ivanov et al., Chemical Abstracts, vol. 84, No. 56142z, 1975.
Muramoto et al., Chemical Abstracts, vol. 89, No. 193356q, 1978.
Reith et al., Biochem. J., vol. 56, pp. 116–120 (1954).
Birr et al., Angew. Chem. Int., vol. 9, No. 9, p. 731, (1970).
Chang et al., Biochem. J., vol. 157, pp. 77–85, (1976).
Hunkapiller et al., Biochem., vol. 17, pp. 2124–2133, (1978).
Laursen et al., Methods of Biochemical Analysis, vol. 26, pp. 201–284, (1980).
L'Italien et al., Anal. Biochem., vol. 127, pp. 198–212, (1982).
G. E. Tarr, in Methods in Protein Sequence Analysis, M. Elzinga, Ed., Humana Press, Clifton, NJ (1982), at 223–232.
J. J. L'Italien et al., J. Biol. Chem., 256, 8092 (1981).
R. M. Hewick et al., J. Biol. Chem. 256, 7990 (1981).
W. R. Gray et al., Anal. Biochem., 33, 36 (1970).
J. Y. Chang et al., Biochem. J., 199, 557 (1981).
P. Edman, in Protein Sequence Determination, S. Needleman, Ed., Springer-Verlag, New York (1970), at pp. 211–255.

*Primary Examiner*—Barry S. Richman
*Assistant Examiner*—Robert J. Hill, Jr.
*Attorney, Agent, or Firm*—Merchant, Gould, Smith, Edell, Welter & Schmidt

[57] ABSTRACT

A protein sequencing method utilizing a composition of matter which comprises a D-C-B-A reagent wherein A is a moiety which can react with and bind to a terminal amino acid of a protein and can result in removal of the terminal amino amino acid, B is a moiety which provides steric separation between C and A, C is a nucleophilic moiety which can be detected, and D is a moiety which protects the C moiety from degradation or other modification, and is labile in acidic media and stable in neutral or basic media. The protein sequencing method and reagent can be used in micro sequencing apparatus.

7 Claims, No Drawings

PROTEIN SEQUENCING METHOD

FIELD OF THE INVENTION

The invention relates to sequencing a polypeptide or protein molecule in order to determine its amino acid sequence. More particularly, the invention relates to a novel composition of matter and a method for the micro sequencing of very small amounts of protein.

BACKGROUND OF THE INVENTION

Proteins (polypeptides) are naturally occurring compounds that are composed of long chains of amino acids. Proteins are found throughout living things and function as hormones, structural elements, enzymes, immunoglobulins, and other constituents of living things. Research regarding the structure and functions of proteins often requires that the amino acid sequence (primary structure) of the protein be determined. In order for a protein or parts of a protein such as somatostatin, insulin, endorphins, etc. to be synthesized the sequence of amino acids must be determined before a synthesis can be attempted. In the search involving the function of proteins such as immunoglobulins, enzymes, viral coat proteins, and cell-surface proteins, the primary structure of the polypeptide must be determined in an attempt to elucidate the mechanism action of the protein.

The primary sequence of amino acids in proteins or polypeptides is commonly determined by stepwise chemical degradation process in which single amino acids are removed one by one from the end of the polypeptide for identification. The Edman degradation is the preferred method, while other methods have been developed and can be used in certain instances. In the Edman degradation amino acid removal from the end of the protein is accomplished by reacting the N-terminal amino acid residue with a reagent which allows selective removal of that residue from the protein. The resulting amino acid derivative is converted into a stable compound which can be chemically removed from the reaction mixture and identified.

Many physiologically active proteins are present in organisms at such extremely small concentrations that only very small amounts of the proteins can be obtained for sequencing analysis. Most current chemical sequencing methods are done with an amount of protein in the 5-100 nanomole ($5 \times 10^{-9}$ to $10^{-8}$ mole) range. It has been reported that micro sequencing of polypeptides by reverse phase high pressure liquid chromatography using ultraviolet light detection means has been accomplished with protein samples in the range of 50-500 picomole ($5 \times 10^{-11}$ to $5 \times 10^{-10}$ mole) range. Other methods used in the micro sequencing of polypeptides involve radio labeling of the peptide or reagent, intrinsic radio labeling of the polypeptide, and enhanced UV detection of sequence degradation products, and others. While we will not discuss the details of these methods, each method has its limitations and restrictions. They have not been used with overall satisfactory results. The current best art is computer-aided UV detection of PTH amino acids from a microsequencer.

Many techniques have been developed in recent years for the analytical separation of polypeptides or proteins having high physiological activity in very low quantities of about $10^{-12}$ mole (1 picomole), about 50 nanograms of a 50,000 molecular weight protein. A sequencing method developed specifically for such small amounts of proteins is desirable.

One detection method which has an inherent sensitivity in the femtomole ($10^{-13}$ to $10^{-15}$ mole) range is fluorescence. Attempts have been made to use fluorescent isothiocyanates in the Edman degradation, however overall success in micro sequencing of small amounts of protein has not been demonstrated to date.

Accordingly a substantial need exists for a micro sequencing reagent and method adapted for the sequencing of amounts of protein in the low picomole to sub-picomole range of protein.

BRIEF SUMMARY OF THE INVENTION

We have found a novel protein micro sequencing reagent which can be used in sequencing to determine the primary structure of very small amounts of protein. The novel micro sequencing reagent comprises a compound having the formula A-B-C-D wherein A comprises a chemical functional group which can be used to react with a terminal amino acid and which after chemical processing can cooperate in the removal of the terminal amino acid from the polypeptide chain. B comprises a moiety which connects group A with group C and can also function as a ultraviolet light absorbing compound and/or as a reactivity-modifying moiety for group A. Group C comprises a moiety capable of detection at extremely low concentration or a moiety which can be reacted with a group capable of providing the low detection limits required in sequencing very small amounts of protein. D is a group which protects the C group from degradation or other undesirable reaction during the reaction of the sequencing reagent with the terminal amino acid. The micro sequencing reagent must be able to react with the N-terminal amino acid and cleave the terminal amino acid from the polypeptide chain. The D group is removed from the reaction product of the amino acid and sequencing reagent exposing the C group which can then be used for further reaction with appropriate detection means, or which can be itself detected.

For amino terminal sequencing:

"A" may be but is not limited to such primary amine-reactive species as —N═C═S, —N═C═O,

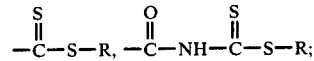

for carboxyl terminal sequencing:

"A" may be but is not limited to such carboxyl reactive species as —R—OH where R may be either an alkyl or aryl group;

For any mode of sequencing:

"B" may be any alkyl chain which may or may not be branched and/or any aryl ring and/or rings with akyl substitution and/or substitutions at the meta and/or para positions;

"C" may be any nucleophilic moiety such as —NH—, —S—, —O— but is not limited to these groups;

"D" may be but is not limited to acid (or base) labile protecting groups such as t-butyloxycarbonyl, benzyl, carbobenzyloxy carbonyl, etc. A wide variety of protecting groups is known in the art.

An aspect of the invention is the protein micro sequencing reagent. A second aspect of the invention is a method for sequencing small quantities of protein using the novel protein micro sequencing reagent of the invention. A third aspect of the invention is a method of preparation of protein micro sequencing reagents.

DETAILED DISCUSSION

A preferred protein micro sequencing reagent comprises a reagent that can be used in the Edman sequencing degradation reactions. The micro sequencing reagent comprises a reagent having the following formula: $(L-NH)_n-R-N{=}C{=}S$ wherein n is an integer, L is a group which is labile in acid but is stable in neutral and basic media, and R is an aliphatic, aromatic, or mixed aliphatic, aromatic group which sterically and electronically separates the nitrogen group from the isothiocyanate group, preserving the desired reactivity. The reagent is designed such that during micro sequencing of a polypeptide the NH group is protected from reaction with the isothiocyanate amine-specific reactive moiety during the initial coupling step of the micro sequencing reagent with the N-terminal amino acid. After coupling is complete and unreacted micro sequencing reagent has been removed the labile L group attached to the amino group can be removed simultaneously with the cyclization step in the sequencing reaction giving a thiazolinone produced in the cleavage of the N-terminal amino acid from the protein. The amino group in acid solution appears as an inert protonated cationic moiety during cleavage and removal of the L group, and during conversion to the thiohydantoin derivative. After chromatographic separation the protonated cationic moiety can be deprotonated and converted to a nucleophilic amino group. The amino group can then be reacted with a fluorogenic reagent such as 4-phenylspiro[furan-2(3H),1'-phthalan]-3,3'-dione(fluorescamine) or o-phthalaldehyde, (OPA) or other fluorogenic reagents. The resulting attached fluorescent moiety can be detected using manual or automated fluorimetry taking advantage of the fluorescent properties of the attached fluorescent moiety.

A preferred L group comprises groups having the formula

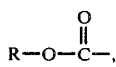

wherein R is a branched chain alkyl, or aryl group having from about 1 to about 20 carbon atoms such as tertiary butyl, tertiary amyl, 1-methylcyclohexyl, biphenylisopropyl, etc. The use of the preferred L group results in micro sequencing reagents which are generally freely soluble in organic solvents commonly used in Edman degradation methods.

While the invention is directed primarily to sequencing of proteins beginning at the N-terminal amino acid, the general approach and many of the variations can also be adapted to sequencing proteins beginning at the C terminal amino acid.

Protein Sequencing

Any peptide or protein which is to be amino terminally sequenced must have a free N-terminal amino acid. Protected or blocked N-terminal amino acids must be converted to free N-terminal amino acids before sequencing can begin. The protein can be sequenced in free solution or on a variety of well known solid support media. Excess sequencing reagent (formula L—NH—[CH$_2$]$_n$—R—NCS) is added to the protein in the presence of base or after neutralization of the amino group to the protein. After sufficient time to insure complete reaction between the sequencing reagent and the N-terminal amino acid, the unreacted reagent and other chemicals or by-products are removed by washing. The resulting reaction product between the sequencing reagent and the protein can have the following formula (II)

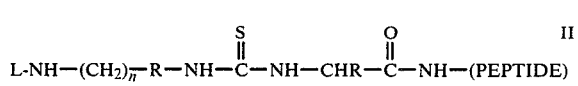

In order to effect cyclization of the reaction product and concommittant cleavage of the N-terminal amino acid from the protein, the reaction product is treated with anhydrous acid. Simultaneously with the cyclization-cleavage, the L group on the amino group is removed, resulting in a species (III) and a free terminal amino acid on the peptide chain which can then be subjected to another cycle of the degradation. The cyclized reaction product is removed from the residual protein by washing with suitable solvents. The washes are collected and the recovered thiazolinone (III) is converted to the stable thiohydantoin (IV), by treatment with aqueous or alcholic acid at elevated temperatures.

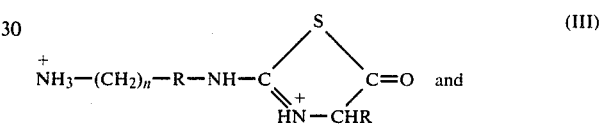

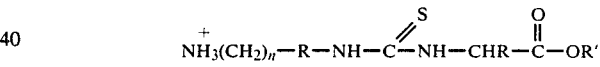

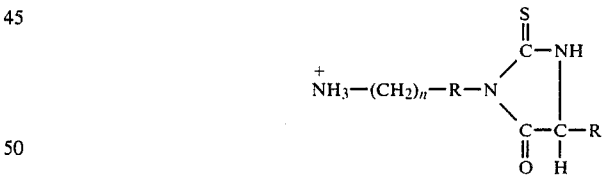

The resulting substituted reaction product (IV) is subjected to chromatographic analysis, most commonly reverse phase high pressure liquid chromatography (HPLC). Subsequent to the separation, the reaction product can be detected by ultraviolet absorbance if desired or preferably can be reacted with a fluorogenic reagent (such as OPA or fluorescamine), under appropriate reaction conditions, and detected by fluorimetry. Both UV and fluorescent detection can be performed in the same experiment, consecutively in the order given. Standard methods, equipment, solvents, buffers, reaction sequences of manual and automatic sequencing can be used with minor modifications where necessary to accomodate the nature of the resulting reaction product. Preferred automated methods include the spinning cup, solid phase, and gas liquid phase sequencing methods. Further, common pre or post-column chromatography derivatization techniques and flow fluorimetry can be used for the fluorescence detection of the reaction product. Adjustment of reaction conditions such as reagent, buffer, pH, flow rate, delay time, excitation, and detection wavelengths may be necessary to optimize sensitivity. The following Examples contain descriptions of two micro sequencing reagents, the use in sequencing proteins, and a best mode.

EXAMPLE I

Synthesis of 4-(tertiary-butyloxycarbonylamino)-phenylisothiocyanate

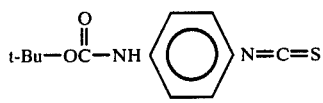

Into a glass Erlenmeyer flask at ambient temperature was placed 1 gram (4.81 millimole) of t-butyloxycarbonyl-1,4-phenylenediamine

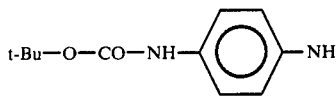

dissolved in 20 milliliters of chloroform. Into the vessel was added 28 milliliters of aqueous 1 M sodium bicarbonate. The aqueous and chloroform phases were rapidly stirred with a magnetic stirrer until the phases were intimately contacted. Into the rapidly stirred biphasic mixture was added 2.21 grams (19.2 millimole) thiophosgene

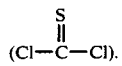

Copious amounts of solid deposited and rapidly redissolved. The mixture was permitted to react at ambient temperature for 2 hours. The reaction was monitored by removing microliter aliquots of the reaction mixture for thin layer chromatography analysis (silica gel GF, 250 micron thickness; developed in $CHCl_3$:MeOH:HOAC, 85:10:5 by volume; visualized by short wave ultraviolet, and by spraying with 0.1% ninhydrin in n-butanol solvent followed by heat. Starting material, having an Rf of 0.45 and instantly visualized by ninhydrin and heat, disappeared giving a principal compound Rf 0.9 slowly visualized by ninhydrin and heat, and a minor compound Rf 0.85. The reaction appeared to be complete within about 15 minutes. After about 2 hours, mixing was terminated and the phases separated. The chloroform layer containing the product was washed with three 20 milliliter volumes of water, dried over anhydrous magnesium sulfate and subjected to rotary evaporation at reduced pressure. (Caution: use of a hood is recommended; thiophosgene vapor is present.) Into the rotary evaporator flask was placed three 10 ml portions of dichloromethane which were removed in turn using reduced pressure. The crude reaction product was a cream color solid, soluble in acetone, methanol, benzene and ethyl acetate, but insoluble in petroleum ether. The liquid product was recrystallized from hot petroleum ether:ethyl acetate (20:2). The resulting white crystalline product was washed with petroleum ether and dried under vacuum. The synthetic route yielded 0.251 grams (21% of theoretical). A repeat run on a 6.8-fold scale gave a 49% yield of the same compound. Infrared analysis showed the strong band at 2100 cm$^{-1}$ characteristic of isothiocyanates, and the band at 1690 cm$^{-1}$ characteristic of urethane carbonyl.

The neutralization of hydrochloric acid liberated during the synthesis of the isothiocyanate is extremely important since the acid can result in the removal of the t-butyloxycarbonyl group. Accordingly, the bi phasic reaction system in which the bicarbonate neutralizes the acid produced in the reaction in the chloroform phase is critical to forming the micro sequencing reagent.

EXAMPLE II

Synthesis of 4-(tertiary butyloxycarbonylaminomethyl) phenyl isothiocyanate

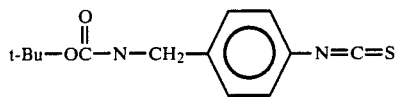

Into a glass Erlenmeyer flask was placed 5 grams (26.5 millimoles) of 4-nitrobenzylamine hydrochloride suspended in 10 milliliters tertiary butanol and 5 milliliters of water. Concentrated aqueous sodium hydroxide 2.16 milliliters (27 millimoles) was added to the suspension followed by 10 milliliters of dimethyl formamide. Into the resulting dark colored solution having some suspended solids was placed 5.8 grams (26.6 millimoles) di-tertiarybutyldicarbonate dissolved in 10 milliliters of tertiary butanol, drop-wise with stirring over a period of 30 minutes. The reaction was allowed to continue overnight. Considerable solid was deposited. At the completion of the reaction the reaction mixture was diluted with 40 milliliters of water and the crude mixture was extracted with three 50-ml volumes of petroleum ether. The aqueous layer, titrated to pH 2 in the presence of ethyl acetate, was extracted with three 60-milliliter portions of ethyl acetate which were combined and dried with anhydrous magnesium sulfate combined with the petroleum ether layers. The crude product, 4(t-butyloxycarbonylaminomethyl)nitrobenzene, obtained from the combined layers were analyzed by TLC chromatography as described above which showed the product (Rf 0.9; slowly ninhydrin positive) to be about 97% pure. The crude solid was dissolved in 50 milliliters of 90% by volume acetic acid in water in a glass Erlenmeyer flask. 8.6 grams of zinc dust (132.5 millimoles) was added to the vigorously stirred solution. The progress of the reaction was monitored chromatography as discussed. The zinc reduction was complete after about 1 hour at ambient temperatures. The starting material (Rf 0.9, slowly ninhydrin-positive) being replaced by a compound of Rf 0.65, instantly ninhydrin-positive. This is the direction of Rf change expected for the change chemical nature; furthermore, the product showed colored decomposition products on silica gel GF, characteristic of an aniline. Two hours after the reaction began the mixture was diluted with 300 milliliters of water, titrated to pH 6 with aqueous sodium hydroxide in the presence of 200 milliliters of ethyl acetate. The aqueous phase was extracted with three 100 milliliter volumes of ethyl acetate. The combined ethyl acetate layers were dried and solvent was removed with a rotary evaporator under reduced pressure yielding a thick yellow oil. The crude 4-(tertiarybutyloxycarbonyl aminomethyl) aniline was converted to the isothiocyanate following the same procedure described in Example I using 40 milliliters chloroform, 60 milliliters 1 molar aqueous sodium bicarbonate, 2.21 grams (19.2 millimoles) thiophosgene. The reaction yielded 1.73 grams of product. The product was freely soluble in acetonitrile and dichloromethane. Infrared analysis showed the characteristic strong isothiocyanate bands at 2100 cm$^{-1}$ and the urethane carbonyl at 1690 cm$^{-1}$.

EXAMPLE III

USE IN SEQUENCING

4(t-butyloxycarbonyl-aminomethyl)phenylisothiocyanate (BAM PITC) was dissolved in acetonitrile at a concentration of 5% (w/v) and placed in the coupling reagent reservoir and delivery system of an unmodified solid phase sequencer (Sequemat Mini 15). The peptide Leu-Ala-Gly-Val-Leu-Ala-Gly-Val-Phe coupled to aminomethyl-copoly(styrene-1% divinylbenzene) resin (15 mg, about 5 nanomoles of peptide) was loaded in a standard 3 mm × 100 mm glass reaction column where it was mixed with sufficient glass beads (240–280 mesh) to prevent clogging of the column. The remainder of the reaction column was filled with the same glass beads. A standard solid phase Edman degradation was performed according to the following protocol:

| Step | Functions | Channel | Time |
|---|---|---|---|
| 0 | Start | 8 | 0–1 |
| 1 | MeOH | 1,8 | 1–5 |
| 2 | Buffer | 3,8 | 5–6 |
| 3 | Buffer/PITC | 3,4,8 | 6–19 |
| 4 | Buffer | 3,8 | 19–23 |
| 5 | MeOH | 1,8 | 23–31 |
| 6 | DCE | 2,8 | 31–35 |
| 7 | MeOH | 1,8 | 35–39 |
| 8 | DCE | 2,8 | 39–43 |
| 9 | MeOH/F.C. | 1,9,8 | 43–45 |
| 10 | TFA/Collect/Reag. Part. | 5 | 45–54 |
| 11 | TFA/Collect/Channel 15/Reag. Part | 5,15 | 54–56 |
| 12 | TFA/Collect/Reag. Part. | 5 | 56–62 |
| 13 | MeOH/Collect | 1 | 62–63 |
| 14 | Rest | 8 | 63–64 |
| 15 | MeOH/Collect | 1 | 64–65 |
| 16 | End | E.P. | 65–0 |

At each cycle of the degradation, the cleaved aminomethyl-amino-thiozolinone derivative was washed from the reaction column in the trifluoroacetic acid used to effect the cleavage, and was collected in a conical glass centrifuge tube (3 mm × 150 mm) in the fraction collector. The delivery line to the fraction collector was washed with methanol which was also collected in the same tube. After completion of the sequencing, the fractions were blown to dryness under a stream of nitrogen at 50° C. 1M HCl in methanol (1 mL) was added and the tubes heated at 65° C. for 10 minutes to effect conversion to the PTH derivative. The samples were again reduced to dryness under a stream of nitrogen at 50° C. For analysis, the residue in each tube was taken up in 300 uL of methanol.

EXAMPLE IV

SEQUENCING 4-(t-butyloxycarbonyl-aminomethyl(phenylisothiocyanate prepared as in Example II was used to sequence the peptide Leu-Ala-Gly-Val-Leu-Ala-Gly-Val-Phe covalently attached to aminomethyl-poly-(styrene-1%·divinylbenzene) resin (15 mg, about 5 nanomole). The procedures described in Example II were followed, with the exception that each cycle the cleaved aminomethyl-anilinothiozolinone in trifluoroacetic acid and the subsequent methanol washes were delivered to the fraction vessel of a standard P-6 auto convertor where the following operations were performed automatically. The TFA and methanol were removed under a stream of nitrogen, conversion to the PTH derivative was effected with 1M HCl in methanol which was subsequently removed under a stream of nitrogen. All operations were performed at 65° C. The resulting PTH derivative was rinsed with several lots of methanol into a conical centrifuge tube in the fraction collector. The standard P-6 program was used. After completion of the sequencing run, the fractions in each tube were reduced to dryness under a stream of nitrogen at 50° C. and the residue taken up in 300 microliters methanol for analysis.

EXAMPLE V

DETECTION

Aniline, benzylamine, and phenethylamine were used as models for the NH$_2$(CH$_2$)$_n$PTH derivatives, where n=0, 1, 2 respectively. Aliquots of these compounds were dissolved in methanol and spotted on TLC plates (silica gel GF, 250, microns) (100, 200, and 500 picomole of each in 1, 2, 5 uL methanol, respectively). The plates were sprayed with buffer and with fluorogenic reagent:

Fluorescamine
 Buffer: 1% triethylamine in acetone (v/v)
 Reagent: 0001% fluorescamine in acetone (w/v)
O-phthalaldehyde
 Buffer: 1% triethylamine +0.05% beta-mercaptoethanol in acetone (v/v)
 Reagent: 10 mg OPA in 33 mL acetone.

The plates were examined under a long wave length UV lamp. The three compounds each gave a bright green fluorescence on a dark purple background after reaction with fluorescamine; this took several minutes to reach maximum intensity and was stable for hours at room temperature. One hundred picomole of each compound was readily detected. With OPA, phenethylamine and benzylamine gave a pale blue fluorescence; this developed very rapidly (seconds) and was not long lived (faded noticeably after 30 minutes). To the eye, the OPA response was lower, with 100 picomoles barely detectable. Aniline did not react with OPA under these conditions.

A combined reagent spray was also used for fluorescamine detection:
Combined Reagent and Buffer for Fluorescamine
 0.001% fluorescamine, plus
 0.01% triethylamine in acetonitrile.

This spray, used on samples of 500 picomole each of aniline, benzylamine, and phenethylamine with fresh reagent gave the same strong green fluorescence under the long wave length UV lamp for each compound as obtained with the separate reagents in acetone. However, 4½ hours after being made up the single spray gave a noticeably higher background which became high enough to significantly interfere when used 7½ hours after being made up.

The PTH derivative from cycle #2 (Ala) of the sequencing in Example 2 was spotted on a TLC plate (as above) (20 uL of 300 uL in methanol; 333 picomole based on 5 nanomole sequenced). Spraying with either fluorescamine or OPA gave a positive response with fluorescence of about the expected intensity compared with the response of an equal amount of benzylamine. The response was much stronger with fluorescamine than with OPA. This indicates that the derivatives obtained from sequencing/conversion contain a free amino group in the expected amount.

HPLC.

Aniline, benzylamine, and phenethylamine were separated by reverse phase HPLC on a C18 micro Bondapak column using an isocratic system consisting of 20% methanol in 10 mM potassium phosphate, pH 2.5, pumping at 0.7 mL per minute. The compounds were detected by UV absorbence at 214 nm, and eluted at 4.93, 5.71, 6.80 minutes, respectively. After passage through the UV detector, the effluent stream was mixed with buffered OPA reagent (475 mL 0.8 M potassium borate, pH 10.5; helium degassed, plus 400 mg OPA in 2mL MeOH+ 1mL beta-mercaptoethanol, kept under helium [fresh daily]) pumping at 0.7 mL/min. The combined effluent stream passed through a delay coil (50 feet of 1/10,000 inch I.D. tubing) to a flow fluorimeter (Gilson Model 121; Corning designation excitation filter 7-60, emission filter 450-7C). Aniline did not fluoresce under these conditions. Benzylamine and phenethylamine gave strong fluorescence signals, with benzylamine giving twice the signal of phenethylamine. Benzylamine gave full scale detection (greater than 18 cm) from a baseline with 1 mm peak-to-peak noise for 50 picomoles injected.

A similar experiment was performed with fluorescamine detection. Aniline and benzylamine were separated by reverse phase HPLC on a C18 micro Bondapak column using an isocratic system consisting of 10% acetonitrile in 10 mM potassium phosphate, pH 5.6, pumping at 1.4 mL per minute. The compounds were detected by UV absorbence at 214 mm. After passage through the UV detector, the effluent stream was mixed with "buffered" fluorescamine reagent (15 mg fluorescamine in 100 mL acetonitrile containing 0.15% (v/v) triethylamine)—used within hours of being made up—pumping at 0.7 mL/min. The combined effluent stream passed through the delay coil described above and was detected in the same flow fluorimeter. Both compounds gave strong fluorescence signals under these conditions.

EXAMPLE VII

Analysis and Detection of Sequencing Products

The aminomethyl-PTH derivatives derived from the sequencing described in Example 2 were analyzed by reverse phase HPLC using two supelcosil C18 analytical columns in series with an isocrate eluant consisting of 33.3% (v/v) acetonitrile, 0.4% (v/v) dichloroethane, in 20 mM sodium acetate, pH 4.7, flow rate 1.2 mL/min. Detection was by UV absorbance at 254 nm. 1/20 of each sample was injected. UV absorbing derivatives were detected in the expected amounts (compared with analysis of an identical sequencer run using PITC reagent). The elution positions were somewhat earlier for the aminoethyl-PTH derivatives compared with the PTH derivatives. This is consistent with the expected effect of an additional ammonium-methylene moiety. Also as expected, the effect was more pronounced for more hydrophobic PTH. See Table. Repetitive stepwise yields for the sequencing run were 0.92, 0.91 based on Ala[2,6], Gly[3,7], respectively. The control run using PITC gave repetitive stepwise yields of 0.91, 0.94. Thus, the Bam-PITC is as efficient as PITC for sequencing under the conditions used.

TABLE

| Amino Acid (Sequencer Cycle) | PITC Run Elution time/Amount (area units) | Bam PITC Run Elution time/Amount (area units) |
|---|---|---|
| Leu (1) | 30.13 min/384 | 16.20 min/432 |
| Ala (2) | 9.65 min/426 | 6.45 min/479 |
| Gly (3) | 7.52 min/500 | 5.70 min/326 |
| Phe (9) | 26.36 min/— | 13.70 min/— |

Large amounts of a UV absorbing impurity were present in some cycles, obscuring parts of the chromatogram. This is typical of the type of impurity occasionally present in sequencing.

A further aliquot (1/30) of the same set of samples was reanalyzed under modified HPLC conditions: C18 microBondapak column, isocratic elution with 10% acetonitrile in 10 mM potassium phosphate, pH 5.65, flow rate 0.80mL/min. Detection was by UV at 254 nm, and subsequently the effluent stream was mixed with "buffered" fluorescamine reagent (15 mg in 100 mL acetonitrile containing 0.15% (v/v) triethylamine kept under an inert atmosphere) at 0.40 mL/min. The combined effluent stream passed through the delay coil and fluorimeter described in Example VI. Filters used were: Corning designation: excitation 7-51; emission 3-71. The UV and fluorescence signals were plotted simultaneously on a two pen integrator/printer/plotter. Strong fluorescence peaks corresponding to the UV absorbance peaks of the aminomethyl-PTH derivatives were observed. Most significantly, the strongly UV-absorbing impurity was overwhelmingly evident in the UV detection channel, but was not detected in the fluorescence signal. This illustrates the particular utility of the Bam-PITC reagent in that the UV absorbing impurity from commonly used sequenator reagents did not appear in fluorescence detection, UV detection can be used for macroscale sequencing and fluorescence detection for microscale sequencing with the same reagent.

While only certain embodiments of our invention have been described in specific detail it will be apparent to those skilled in this art that other specific embodiments may be practiced, and many changes may all be made within the spirit of the invention, and it is intended that all such embodiments and changes be considered within the scope of the invention which resides wholly within the claims hereinafter appended.

We claim:

1. A method for the determination of the identity of a terminal amino acid of a polypeptide which comprises:
    (a) reacting a terminal amino acid of a polypeptide with a composition of matter which comprises D-C-B-A reagent to form a reagent-derivatized terminal amino acid, wherein A is a moiety which can react with and bind to a terminal amino acid of a polypeptide molecule and can result in removal of the terminal amino acid; B is a moiety which provides steric separation between C and A; C is a nucleophilic moiety selected from the group consisting of —NH—, —S— or —O— which can be detected directly or which can be derivatized with a group that can be detected; and D is a moiety which protects the C moiety from degradation or other modification, and which is labile in acidic media and stable in neutral or basic media;

(b) causing the reagent-derivatized terminal amino acid to cleave from the polypeptide to form a cleaved DCBA reagent-derivatized amino acid;

(c) chemically removing the D moiety from the cleaved DCBA reagent-derivatized amino acid by acidification thereof; and (d) detecting the presence of the C moiety on the CBA reagent-derivatized amino acid.

2. The method of claim 1 wherein the CBA reagent-derivatized amino acid is chromatographed prior to step (d).

3. The method of claim 1 wherein the presence of the C moiety is detected using fluorescent means.

4. The method of claim 3 wherein the C moiety can be detected at quantities of about $10^{-12}$ to $10^{-15}$ mole.

5. The method of claim 1 wherein the presence of the C moiety is detected by reacting the C moiety with a compound that can be detected using fluorescent means.

6. The method of claim 5 wherein the compound that is reacted with the C moiety can be detected at quantities of about $10^{-12}$ to $10^{-15}$ mole using fluorescent means.

7. The method of claim 5 wherein the detectable CBA-reagent derivatized amino acid is chromatographed prior to detection.

* * * * *

UNITED STATES PATENT AND TRADEMARK OFFICE
CERTIFICATE OF CORRECTION

PATENT NO. : 4,548,904
DATED : October 22, 1985
INVENTOR(S) : STEPHEN B. H. KENT and JAMES J. L'ITALIEN It is certified that error appears in the above-identified patent and that said Letters Patent is hereby corrected as shown below:

Item [73], "Molecular Genetics Research & Development" should read --Molecular Genetics Research & Development Limited Partnership--.
Item [57], in line 5 of the Abstract, for "amino amino" read --amino--.
Column 2, line 57, for "akyl" read --alkyl--.
Column 4, line 27, for "alcholic" read --alcoholic--.
Column 4, line 40, for "NH$_3$" read --NH$_3^+$--.
Column 4, line 47, for "NH$_3$" read --NH$_3^+$--.
Column 8, line 34, for "0001%" read --0.001%--.

Signed and Sealed this

Eighteenth Day of March 1986

[SEAL]

Attest:

DONALD J. QUIGG

Attesting Officer

Commissioner of Patents and Trademarks